(12) United States Patent
Peters et al.

(10) Patent No.: US 10,962,455 B2
(45) Date of Patent: Mar. 30, 2021

(54) METHOD FOR TESTING THE RIGIDITY OF A DISPOSABLE

(71) Applicant: FRESENIUS MEDICAL CARE DEUTSCHLAND GMBH, Bad Homburg (DE)

(72) Inventors: Arne Peters, Bad Homburg (DE); Christoph Wiktor, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 186 days.

(21) Appl. No.: 15/781,216

(22) PCT Filed: Dec. 1, 2016

(86) PCT No.: PCT/EP2016/002033
§ 371 (c)(1),
(2) Date: Nov. 5, 2018

(87) PCT Pub. No.: WO2017/092870
PCT Pub. Date: Jun. 8, 2017

(65) Prior Publication Data
US 2019/0137372 A1    May 9, 2019

(30) Foreign Application Priority Data

Dec. 2, 2015  (DE) .................. 10 2015 015 636.5

(51) Int. Cl.
*G01N 3/12* (2006.01)
*A61M 1/16* (2006.01)
(Continued)

(52) U.S. Cl.
CPC ................ *G01N 3/12* (2013.01); *A61M 1/14* (2013.01); *A61M 1/1635* (2014.02); *A61M 1/34* (2013.01);
(Continued)

(58) Field of Classification Search
CPC .......... A61M 2205/15; A61M 2205/33; A61M 2205/70; A61M 2205/705; A61M 2209/02; G01F 17/00
See application file for complete search history.

(56) References Cited

U.S. PATENT DOCUMENTS

| 3,916,673 A | 11/1975 | Gass et al. |
| 4,534,208 A * | 8/1985 | Macin ..................... G01M 3/10 455/226.1 |

(Continued)

FOREIGN PATENT DOCUMENTS

| DE | 3923078 C1 * | 9/1990 | .......... A61M 1/1684 |
| DE | 19757523 | 4/1999 | |

(Continued)

OTHER PUBLICATIONS

Machine translation of TW-330692 which originally published on Apr. 21, 1998. (Year: 1998).*

(Continued)

*Primary Examiner* — David A. Rogers
(74) *Attorney, Agent, or Firm* — Jacobson Holman PLLC

(57) ABSTRACT

A method for testing the rigidity of a particular disposable for volumetric balancing, for a blood treatment device. The method includes filling the disposable or portion thereof with a liquid, enclosing the filled liquid, so that a certain volume of liquid is present in the disposable unit or the portion thereof, supplying and/or discharging a certain volume of liquid, and measuring the change in pressure caused by the supply and/or discharge of the volume of liquid. A blood treatment device is also provided.

14 Claims, 6 Drawing Sheets

(51) Int. Cl.
*A61M 1/34* (2006.01)
*A61M 1/14* (2006.01)

(52) U.S. Cl.
CPC .......... *A61M 1/341* (2014.02); *A61M 1/3403* (2014.02); *A61M 2205/12* (2013.01); *A61M 2205/15* (2013.01); *A61M 2205/3331* (2013.01); *A61M 2205/3337* (2013.01); *A61M 2205/70* (2013.01); *G01N 2203/0089* (2013.01)

(56) References Cited

U.S. PATENT DOCUMENTS

| | | | | |
|---|---|---|---|---|
| 4,888,718 | A * | 12/1989 | Furuse | G01F 17/00 702/50 |
| 5,319,979 | A * | 6/1994 | Abrahamson | G01L 9/006 73/723 |
| 5,542,919 | A * | 8/1996 | Simon | A61M 1/28 417/395 |
| 5,580,460 | A * | 12/1996 | Polaschegg | A61M 1/3403 210/646 |
| 5,836,908 | A * | 11/1998 | Beden | A61M 1/1668 604/29 |
| 6,066,261 | A * | 5/2000 | Spickermann | A61M 1/1601 210/739 |
| 6,280,632 | B1 * | 8/2001 | Polaschegg | A61M 1/3462 210/103 |
| 6,623,420 | B2 | 9/2003 | Reich | A61M 1/1086 600/17 |
| 6,826,957 | B2 * | 12/2004 | Martone | G01M 3/3236 73/40.5 R |
| 6,993,957 | B2 * | 2/2006 | Kano | F02M 25/0818 73/49.7 |
| 8,402,818 | B2 * | 3/2013 | Bernard | G01M 3/3272 73/49.7 |
| 8,877,061 | B2 * | 11/2014 | Lovell | A61M 1/1621 210/117 |
| 9,352,282 | B2 * | 5/2016 | Fulkerson | A61M 1/1692 |
| 9,474,842 | B2 * | 10/2016 | Childers | A61M 1/28 |
| 9,545,469 | B2 * | 1/2017 | Curtis | A61M 1/1601 |
| 9,572,919 | B2 * | 2/2017 | Kelly | A61M 1/3417 |
| 10,022,673 | B2 * | 7/2018 | Fulkerson | B01D 61/145 |
| 10,137,233 | B2 * | 11/2018 | Sternby | B01D 61/32 |
| 10,441,697 | B2 * | 10/2019 | Kamen | B01D 61/32 |
| 10,537,671 | B2 * | 1/2020 | Wilt | A61M 1/3672 |
| 2005/0000273 | A1 * | 1/2005 | Hosoya | F02M 25/0818 73/49.7 |
| 2007/0068227 | A1 * | 3/2007 | Tsuyuki | F02M 25/0809 73/49.7 |
| 2013/0028788 | A1 | 1/2013 | Gronau et al. | |
| 2013/0292312 | A1 * | 11/2013 | Heide | A61M 1/1647 210/137 |
| 2014/0194820 | A1 * | 7/2014 | Gray | A61M 5/14224 604/153 |
| 2014/0224736 | A1 * | 8/2014 | Heide | A61M 1/1635 210/646 |
| 2014/0276421 | A1 | 9/2014 | Phahey et al. | |
| 2017/0112990 | A1 * | 4/2017 | Heide | A61M 1/3663 |
| 2017/0368252 | A1 * | 12/2017 | Grant | A61M 1/365 |

FOREIGN PATENT DOCUMENTS

| | | | |
|---|---|---|---|
| DE | 102009058681 | 6/2011 | |
| DE | 102011108784 | 1/2013 | |
| EP | 0687474 | 12/1995 | |
| EP | 3040691 A1 * | 7/2016 | ............. G01F 17/00 |
| GB | 1534406 A * | 12/1978 | ................ B65B 3/24 |
| JP | 2009240825 A * | 10/2009 | .......... A61M 1/1601 |
| JP | 2012196301 A * | 10/2012 | |
| TW | 330692 A1 * | 4/1998 | |

OTHER PUBLICATIONS

Official translation of Taiwanese Patent TW-330692 which originally published on Apr. 21, 1998. (Year: 1998).*

* cited by examiner

METHOD FOR TESTING THE RIGIDITY OF A DISPOSABLE

BACKGROUND OF THE INVENTION

1. Field of the Invention

The present invention relates to a method for testing the rigidity of a particular volumetric balancing disposable for a blood treatment device.

The present invention further relates to a blood treatment device.

2. Description of the Related Art

From the state of the art, it is known that blood treatment devices not only carry out blood purification or other treatments, such as separation into different components, for instance, but also, in a further essential task, balance fluid volumes. Haemodialysis, peritoneal dialysis, plasma separation devices, liver support systems and devices used in the context of sepsis may be mentioned as examples of such devices.

Haemodialysis apparatuses thus perform blood treatment by way of the dialyzer, with quantification made of the dialysis fluid volumes supplied to and discharged from the dialysis by means of a balancing system.

For this, volume balance systems are used that have a chamber with a fixed volume in which a flexible membrane is located. The membrane separates the chamber into two areas. If a region is filled with a liquid, the same volume is displaced out of the other chamber. The rigid vessel forming the chamber ensures the desired accuracy, since its volume does not change, due to the rigid chamber walls.

In order to build compact, highly integrated systems, it is desirable to implement similar systems in a disposable, i.e. with a disposable unit.

The volume of the disposable acts as a micro batch, i.e. it can be used for volumetric balancing without being provided a balancing chamber specifically formed for this purpose. For example, the flow paths including the pre-filter of a cartridge, i.e. of the disposable, can together form the batch volume used for balancing.

This type of disposable usually consists of plastic material.

To be able to provide the required balancing accuracy, the convolutions of the disposable must exhibit sufficient rigidity, i.e. inflexibility. This is taken to mean that the convolutions of the disposable are designed so that the volume delimited by it is constant, or lies within the range of certain limits.

Systems and disposables whose rigidity is constant, or within a certain tolerable range, are thus advantageous.

SUMMARY OF THE INVENTION

The objective of the present invention is to provide a method by which the rigidity of wall portions of a disposable, or parts thereof, can be measured.

This objective is resolved by a method for testing the rigidity of a particular disposable for volumetric balancing, for a blood treatment device.

According to this, it is envisaged that the method comprises the following steps: filling the disposable or part thereof with a fluid; enclosing the fluid filled, so that in the disposable unit, or in part of it, a certain fluid volume is present; supplying and/or removing of a certain fluid volume; and measuring the pressure change caused by the supply and/or discharge of said fluid volume.

According to the invention, a certain volume of the disposable, hereinafter also referred to as cartridge, is occluded, i.e. stopped up, which can be done by clamps or valves, for example. One or more short pump pulsations are then carried out, by means of a pump, for example. The more rigid the cartridge, the greater the pressure increase or decrease in the volume enclosed by the cartridge, which is caused by the pump pulsations.

If the cartridge is very rigid, i.e. a constant volume, larger increases or decreases in the measured pressure result than with a cartridge whose walls are flexible, thereby allowing a greater volume change.

The rigidity measurement is influenced by many factors that can per se produce a volume change, such as air unduly present in the disposable after filling with fluid. If the test results in a low rigidity, the filling/flushing process can be repeated as an initial remedial measure, so that any air pocket interference can be excluded. If, in one or more repetitions of the test, or of the method according to the invention, the rigidity threshold value is not achieved, then it can be concluded that the condition of the cartridge wall or disposable is defective.

The rigidity threshold can be selected so that small volume changes, due to air pockets, or defective cartridge walls, or disposable conditions not exceeding the tolerated margin of error are still accepted. This may be the case, for example, when the error with respect to the total fluid volume conducted over the treatment period through the cassette or disposable is <10 or <2 parts per thousand. In this case, the cassette or disposable can nevertheless be described as working.

The method according to the invention is carried out prior to patient treatment with the blood treatment device, preferably directly after filling the disposable. The patient's fluid is connected with the blood treatment device during the implementation of the method. The patient is preferably not connected to the blood treatment device during the procedure.

A case also covered by the invention is that where no fluid volume can be supplied or discharged, i.e. the cartridge is completely rigid, and thereby does not allow for any volume change.

In order to pass the test according to the inventive method, the pressure measured thereby must change in amplitude, i.e. the measured pressure rise or drop must be greater than a reference value. This reference value has been determined in advance as a volumetric balancing with a sufficient value.

The term "measurement of a change in pressure" is also understood as the case where the pressure change per se is not measured, but rather, pressure values are measured and the difference, i.e. the pressure change, is determined. The same applies to terms concerning measurement of a pressure increase or decrease.

It is possible for the supply and removal of fluid volume to occur by means of one or more pumps, which are in fluid communication with the disposable, so that the fluid volume can be supplied or removed from inside the disposable.

For the pump or pumps, these are preferably pumps that already form part of a blood treatment device, which thereby provides the advantage of not having to provide pumps specially intended for carrying out the process.

It is possible for this pump to be the ultrafiltration pump or dialysate pump of a dialysis device.

However, the invention is not limited to dialysis devices. Any other blood treatment devices are encompassed by the invention, such as plasma separation devices, liver support systems, systems for the treatment of sepsis, and so on.

In one possible embodiment of the invention, the method is carried out so that the supply and/or removal of further fluid volume, as well as measurement of the pressure increase or decrease, is carried out several times.

It is possible thereby that the same fluid volume, or also different fluid volumes are always supplied and discharged. In this way, interference effects can be avoided.

Occlusion, that is, impingement of the fluid, can take place by closing valves or clamps, for example. The valves or clamps are preferably those of the blood treatment device.

A further embodiment of the invention provides for the disposable comprising at least two balancing chambers, with at least one channel connecting the balancing chambers provided. Thereby, though the method according to the invention, the chambers, in operation, separated from each other, can simultaneously be tested for rigidity.

In a further embodiment of the invention, the pressure is measured at the pump or in a region of the disposable.

Basically, pressure measurement can take place at any position at which the supply or removal of the fluid volume leads to a pressure change correlating with the rigidity of the disposable.

The present invention further relates to a blood treatment device having at least one receptacle for a disposable intended for volumetric balancing, whereby the blood treatment device includes one or more actuators, which are designed to act on the disposable, whereby the blood treatment device has one or more pumps, which are designed to promote a certain fluid volume in and/or out, and whereby the blood treatment device comprises one or more pressure sensors formed so as to measure the fluid pressure contained in the disposable, whereby the blood treatment device has at least one processor activating the actuator or actuators and one or more pumps, and is programmed to carry out a method that includes filling the disposable or portion thereof with a liquid, enclosing the filled liquid so that a certain volume of liquid is present in the disposable unit or portion thereof, supplying and/or discharging a certain volume of liquid, and measuring the pressure change caused by the supply and/or discharge of the volume of liquid.

As stated above, the blood treatment device may be a dialyzer or plasma separation device, for example, or a liver support system or a device for the treatment of sepsis.

The pump may be the ultrafiltration pump, or dialysate pump or any other blood treatment device pump.

The use of a separate pump, that is, of a pump that does not form part of the blood treatment device is also possible and covered by the invention.

The pressure sensor serving to detect pressure changes is preferably located in or on the pump, or in or on the disposable.

It is further possible for the blood treatment device to include one or more valves, by means of which a certain fluid volume in the disposable can be shut off.

In a further embodiment of the invention, the blood treatment device has an evaluation unit, which is designed to compare the measured pressure increase or decrease with a threshold value.

In this, it is also possible for the blood treatment device to includes a display unit, which is adapted to indicate whether the pressure change measured exceeds a threshold value, or not.

Alternatively or additionally, the blood treatment device can include a locking unit, which is configured to prevent the blood treatment device from operating if the pressure change measured does not reach or exceed the threshold.

In this way, blood treatment with a disposable that does not meet the desired rigidity requirements can be restricted.

BRIEF DESCRIPTION OF THE DRAWINGS

Further details and advantages of the invention will be explained with reference to the embodiment displayed in the Figures.

These display.

In the figures, identical or functionally identical parts are designated by identical reference characters.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
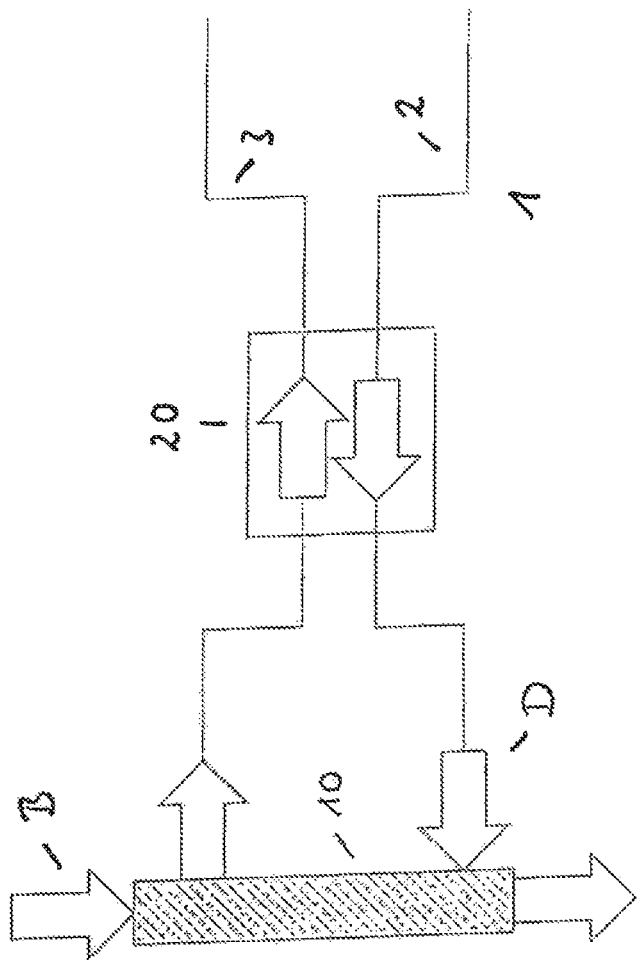
FIG. 1: a schematic view of a dialyzer with a disposable as a balancing system.

FIG. 1 shows a cartridge designed as disposable as reference number 1, used in a dialyzer, not illustrated.

For the dialysis device, the dialyzer is shown by reference number 10, the interior of which is divided by a membrane consisting of a hollow fibre bundle in a dialysate compartment and a blood chamber. The blood chamber comprises the interior spaces of the hollow fibres.

The blood flow through dialyzer 10 is identified by reference B and the dialysate through cassette 1 and through dialyzer 10 is identified by reference D.

The dialyzer can be a haemodialysis, hemofiltration or haemodiafiltration device, for example. However, any other blood treatment devices are included for the invention.

Cartridge 1 includes Channels 2 and 3, and chambers for directing and balancing fresh and spent dialysis fluids.

The chambers of cartridge 1, serving for balancing, are together characterized as reference 20. The balancing system, 20, is configured such that the volume displaced from one chamber corresponds with the dialysis fluid volume supplied to the other chamber. The confirmation of the chambers is performed by dialysis device actuators. Furthermore, the dialysis device features plungers, clamps or other actuators that act as valves, and are able to lock the cartridge channels.

To carry out a rigidity test rigidity test according to the present invention, a volume of Cartridge 1 is shut off by closing the valves, i.e. by disconnecting the cartridge 1 channels, for example.

A specific fluid volume is thus occluded.

For example, valves in feed channels and discharge ports 2 and 3 for the dialysis fluid and between balancing system 20 and dialyzer 10, as well as on the side facing away from the dialyzer of the balancing system will be closed, so that the volume located in between is occluded.

Figure 2:
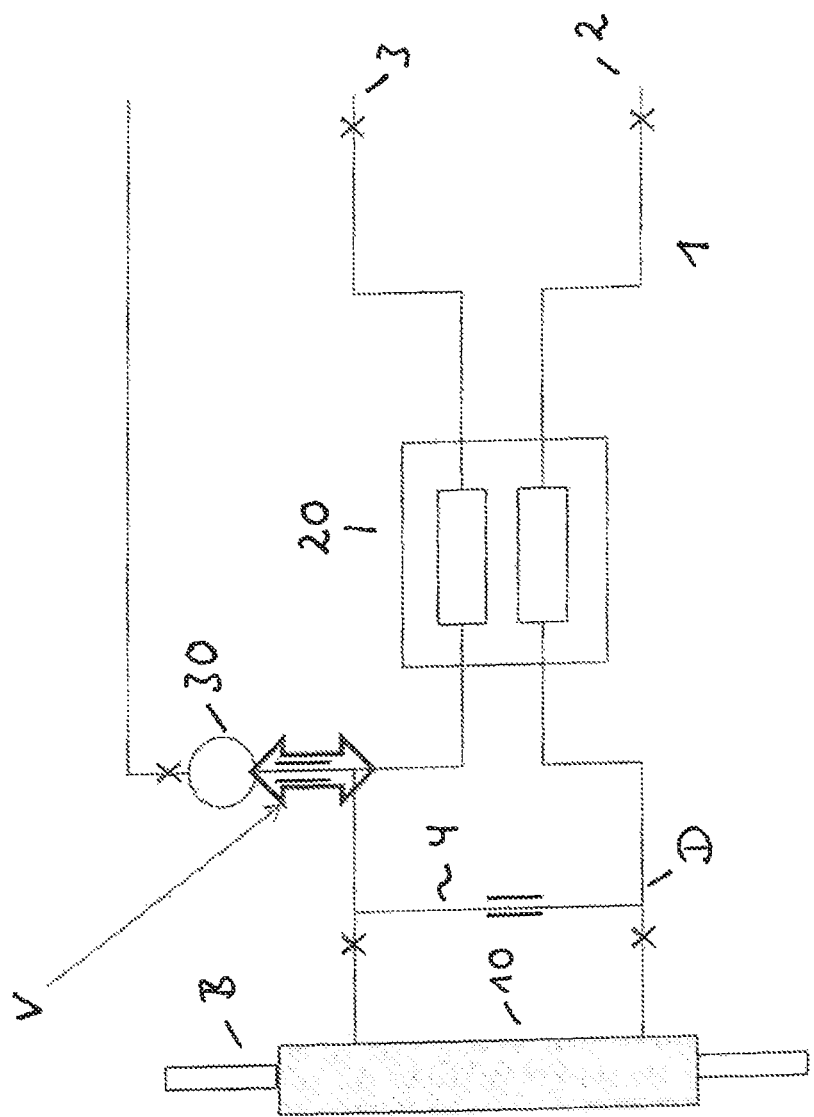
FIG. 2: a schematic view of a dialyzer according to FIG. 1 with an ultrafiltration pump for supplying a further fluid volume, as well as with a connecting line for connection of the channels to be tested.

Such a situation results in FIG. 2. In FIG. 2, closed channels of cartridge 1 or closed valves are marked "x". An open channel or an open valve is characterized by the numeral "II". The same applies to the other figures.

The channel not shut off, or connecting line 4, connects input and output channels 2 and 3 together.

The ultrafiltration pump of the dialysis device is identified by reference number 30.

This is associated with the interior of the cartridge 1 via an open channel, such that the dialysate used in operating the dialysis device is removed from cartridge 1.

To carry out the rigidity tests according to the invention, the ultrafiltration pump 30 is used to carry out a known volume displacement in the occluded hydraulic system of cartridge 1. This volume displacement may consist of a supply and/or withdrawal of liquid to or from cartridge 1.

The rigidity of the walls of cartridge 1 are indicated by measurement of the pressure inside cartridge 1.

The more yielding the cartridge, 1, i.e. the lower the rigidity of cartridge 1, the lower the pressure changes, which are caused by a volume displacement. The stiffer the cartridge, 1, i.e. the higher the rigidity of cartridge 1, the greater the pressure changes, which are due to a volume displacement.

The measured pressure change is thus a measure of the rigidity of the part of cartridge 1 in which the volume is occluded.

In the case outlined in FIG. 2, the ultrafiltration pump 30 exerts the volume shift. However, any other pump that can bring about a volume change in cartridge 1 is suitable for this purpose. It may be a dialysis device pump, or a pump used specifically for determining rigidity.

Figure 3:
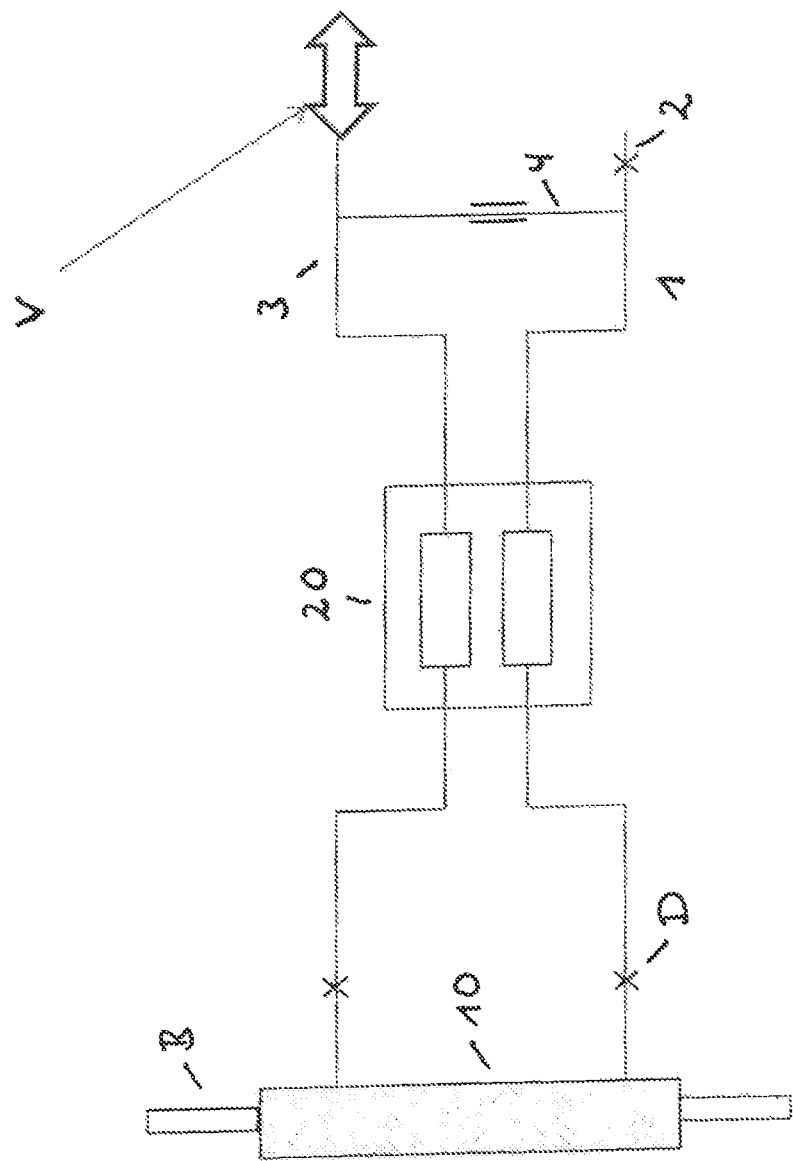
FIG. 3: a further schematic view of a dialyzer according to FIG. 1, with an altered pump arrangement as compared with FIG. 2, and altered cable connection arrangement as compared with FIG. 2 for connection of the channels to be tested.

FIG. 3 illustrates a further embodiment. In this, Channel 4, linking channels 2 and 3, is located not between the balancing system 20 and the dialyzer, but on the side of the balancing system 20 facing away from the dialyzer.

Further deviating from the arrangement, according to FIG. 2, channel 3 is only shut off through a valve. This is located between balancing system 20 and the dialyzer 10. On the other, open side of the channel, 3, is a dialysate, not illustrated, which carries out the volume displacement V in cartridge. 1

A comparison between FIGS. 2 and 3 demonstrates that the position of the shut-off valve "x" and the open channel 4 is not critical. Rather, the decisive factor is that a closed volume of fluid is constituted in the interior of the cartridge 1, open only to the pump, which, through the pump or such like, an additional fluid volume is supplied or a certain volume discharged by means of the pump or such like.

Figure 4:
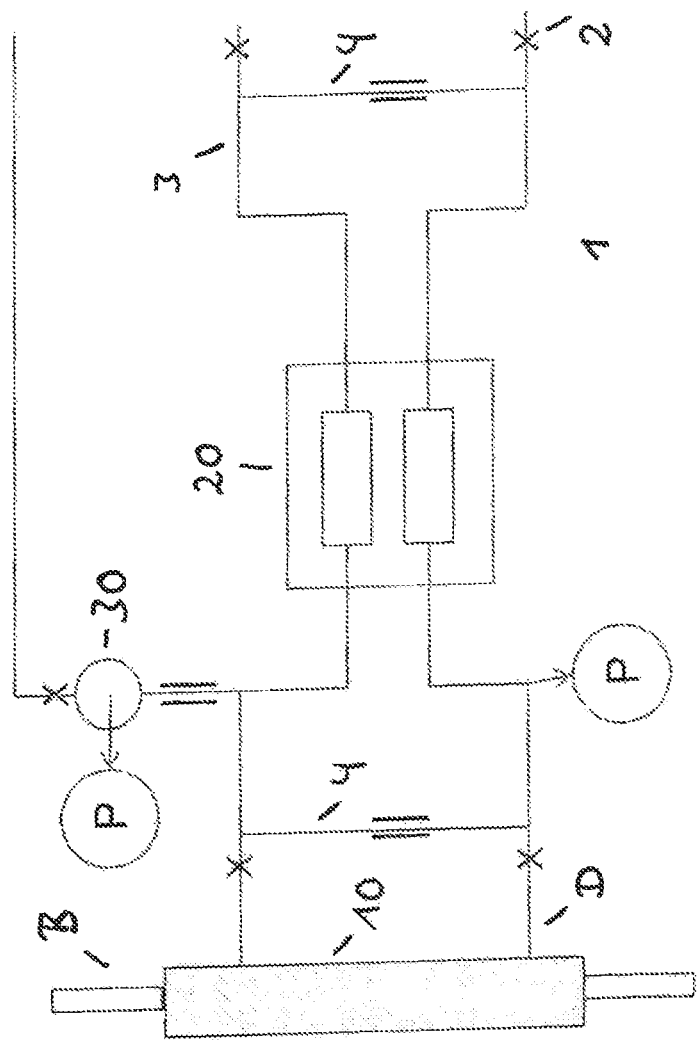
FIG. 4: a further schematic view of a dialyzer according to FIG. 1 with two connecting lines for connecting the channels to be tested, along with possible pressure sensor arrangements.

FIG. 4 shows an embodiment in which a channel 4, connecting channels 2 and 3, is arranged both between the balancing system 20 and the dialyzer 10, and also on the side facing away from the dialyzer 10 side of the balancing system 20.

Furthermore, pressure sensors are indicated by reference P, which measure the pressure in the occluded volume of cartridge 1. As can be seen from FIG. 4, such a sensor P may be located at either the pump 30 or one of the channels 2 or 3.

Other locations for pressure measurement are also possible, and encompassed by the invention. It is thus possible, for example, to measure pressure in the balancing system 20.

The one or more pressure sensors have the task of measuring the volume shift induced pressure change in the occluded fluid volume.

Figure 5:
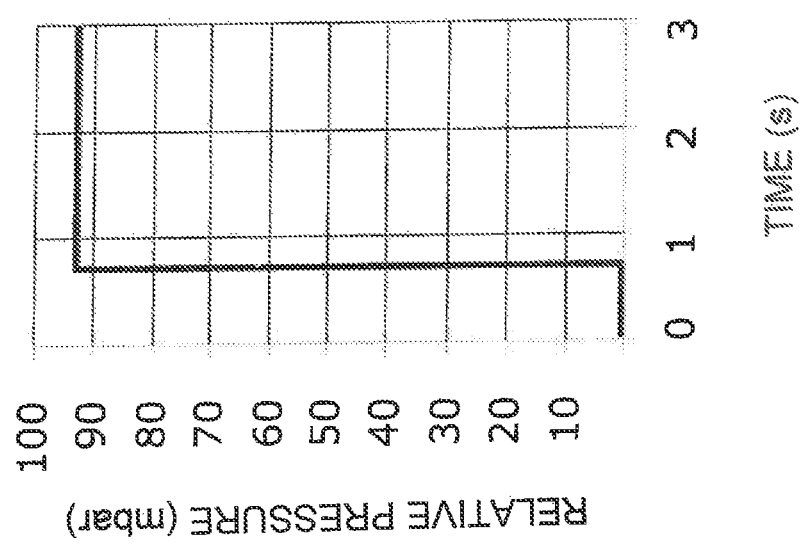
FIG. 5: a view of the pressure course over time with a volume-specific shift

FIG. 5 shows an example of a pressure measurement before, during and after the supply volume in the occluded area of the cartridge as a relative pressure with respect to atmospheric pressure.

In the example illustrated in FIG. 5, there is a pressure increase of approximately 93 mbar from supplying a fluid volume into the occluded area.

When the pressure exceeds a defined limit within the test time, such as the value of 80 mbar within 1 s, the rigidity test is passed and the cartridge 1 is found to be good. If the limit is not reached at all or exceeded only after expiry of the test period, the rigidity test is failed and the cartridge 1 is discarded.

Figure 6:
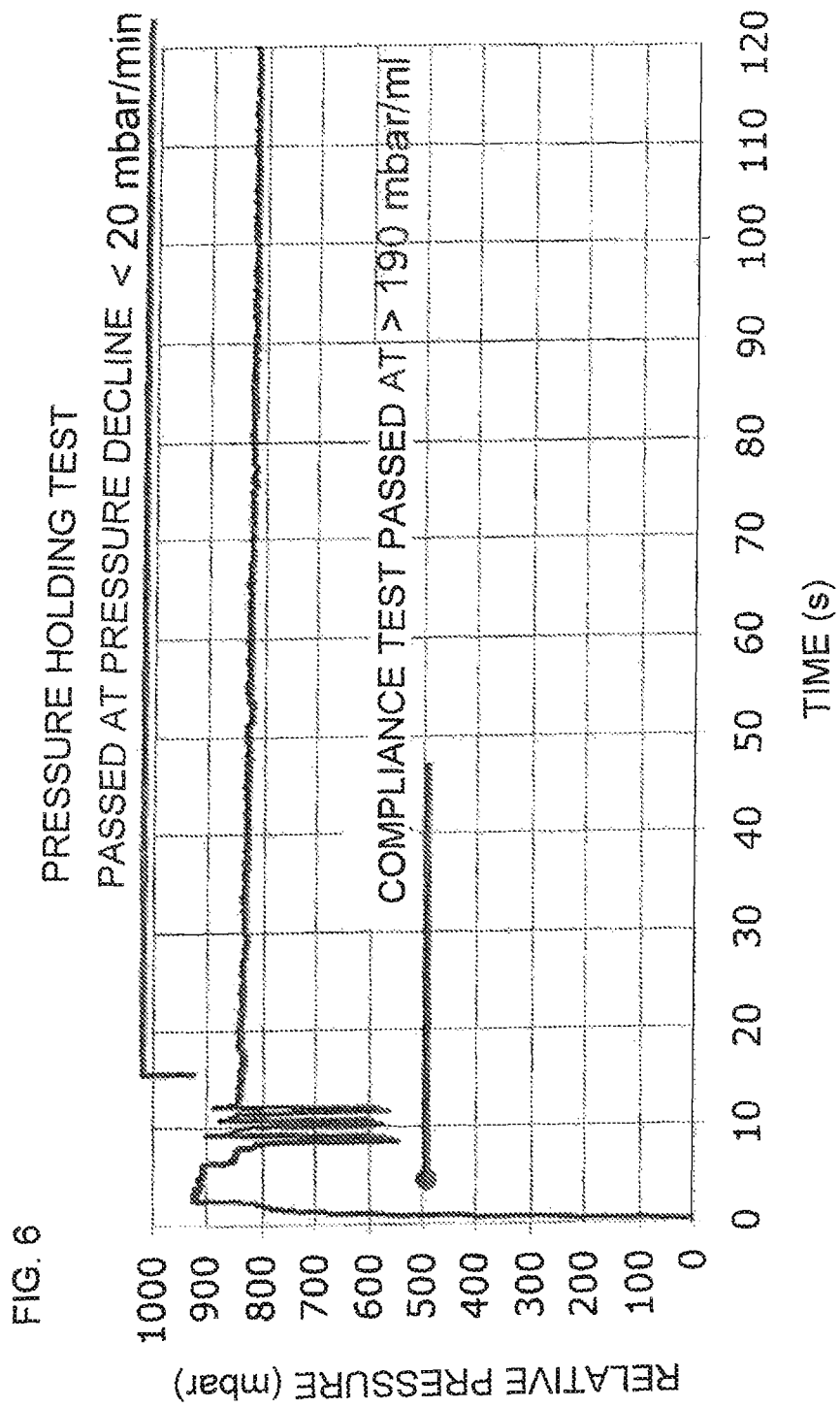
FIG. 6: a view of the pressure course over time for several successive shifts in volumes, and for a pressure holding test.

FIG. 6 shows the pressure curve computed when carrying out a procedure referred to as the compliance test according to the invention.

The pressure curve shown in FIG. 6 is based on a method in which an initial filling of cartridge 1 is made, so that the pressure reaches a certain level (in this case about 900 mbar).

A displacement volume of 1.5 ml is then made into and out of the closed system of cartridge 1.

As seen in FIG. 6, the deduction of volume from cartridge 1 leads to a reduction in pressure of about 550 mbar, and the supply of volume into cartridge 1, to a pressure increase of about 900 mbar. The pressure change, due to the volume displacement, of about 350 mbar is sufficient, since it exceeds the threshold of 190 mbar/ml.

The above values are examples, and not limitative.

The changing volume shift (change from fluid supply and fluid discharge) excludes disruptive effects.

The rigidity test according to the invention is combined with a pressure holding test, according to FIG. 6.

After performing the rigidity tests, no further fluid volume is supplied or removed, and the pressure is further measured.

If the pressure drop over time is below a threshold (here, 20 mbar/min), the pressure holding test is passed. The pressure holding test is based on a certain rigidity of the cartridge. If this is more flexible, the test time and permissible threshold should be adjusted.

The method according to the invention, i.e. the rigidity test, can be carried out before treatment or by commissioning the dialysis device. It can also be carried out during treatment and be triggered by one or more different circumstances.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for testing a rigidity of a particular disposable for volumetric balancing, for a blood treatment device, comprised of the following steps:

filling the disposable or portion thereof with a liquid, said disposable or portion thereof being made of a plastic material and having at least two balancing chambers connected to one another by connecting channel, said connecting channel being coupled to a pressurizing pump;

enclosing the filled liquid so that a certain volume of liquid is present in the disposable unit or portion thereof;

supplying to and/or discharging a certain volume of pressurizing liquid from the disposable using the pressurizing pump, the balancing chambers and the connecting channel being located between valves which are operated so that the pressurizing liquid is isolated from remaining portions of the blood treatment device;

measuring a pressure change caused by the supply and/or discharge of the volume of pressurizing liquid to determine whether the rigidity of the particular disposable is acceptable for use with the blood treatment device, a more rigid disposable producing larger increases or decreases in said measured pressure change than a disposable with wall portions that are more yielding and thus allow a greater volume change.

2. The method according to claim 1, wherein the pressurizing pump is a pump of a blood treatment device.

3. The method according to claim 2, wherein the pump is the ultrafiltration or dialysate pump.

4. The method according to claim 1, wherein the method is carried out before, after or simultaneous with a pressure holding test.

5. The method according to claim 1, wherein the supply and/or discharge of the volume of pressurizing liquid, along with the measurement of pressure change, is carried out multiple times.

6. The method according to claim 1, wherein the enclosing of liquid takes place by closing of the valves.

7. The method according to claim 1, wherein the pressure measurement takes place in or on the pressurizing pump, or in or on an area of the disposable.

8. The method according to claim 1, wherein the disposable passes the rigidity test, and may be used with the blood treatment device, when the measured pressure change exceeds a defined threshold within a defined test period.

9. A blood treatment device comprising at least one input disposable intended for volumetric balancing, said disposable being made of a plastic material, said blood treatment device including one or more actuators that are configured to act on the disposable, one or more pumps that are designed to send a certain volume of liquid into and/or out of the disposable, one or more pressure sensors that are designed to measure the pressure of the liquid contained in the disposable, an evaluation unit that is designed to compare a change in the measured pressure with a threshold, and a locking unit that is designed to prevent the operation of the blood treatment device when the change in the measured pressure does not reach or exceeds the threshold, said blood treatment device further including at least one processor controlling at least one pump and being programmed to fill the disposable or portion thereof with a liquid, enclose the filled liquid so that a certain volume of liquid is present in the disposable unit or portion thereof, supply and/or discharge a certain volume of liquid, and measure the pressure change caused by the supply and/or discharge of the volume of liquid to determine whether the particular disposable is acceptable for use with the blood treatment device, a more rigid disposable producing larger increases or decreases in said measured pressure change than a disposable with wall portions that are more yielding and thus allow a greater volume change.

10. The blood treatment device according to claim 9, wherein the pump is the ultrafiltration pump or dialysis pump of the blood treatment device.

11. The blood treatment device according to claim 9, wherein the pressure sensor is located in or on the pump or in or on the disposable.

12. The blood treatment device according to claim 9, wherein the blood treatment device has one or more valves, by means of which a certain volume of liquid can be shut off in the disposable.

13. The blood treatment device according to claim 9, wherein the evaluation unit is designed to display whether the pressure change measured has exceeded the threshold or not.

14. The blood treatment device according to claim 9, wherein the evaluation unit is designed to compare a speed of the pressure change measured with a threshold.

* * * * *